United States Patent [19]
Felix et al.

[11] Patent Number: 5,925,795
[45] Date of Patent: Jul. 20, 1999

[54] PROCESSES FOR THE PREPARATION OF ARYL-β-DIKETONES, ARYLPYRIMIDINE KETONES AND CROP PROTECTION INTERMEDIATES

[75] Inventors: Raymond A. Felix, Richmond; Hsiao-Ling M. Chin, Moraga; Frank X. Woolard, Greenbrae; David L. Lee, Pleasant Hill, all of Calif.

[73] Assignee: Zeneca Limited, United Kingdom

[21] Appl. No.: 08/715,292

[22] Filed: Sep. 16, 1996

[51] Int. Cl.⁶ .......................... C07C 45/00; C07C 49/76; C07C 65/00
[52] U.S. Cl. .......................... 568/314; 568/319; 568/335; 562/473
[58] Field of Search ........................... 568/314, 319, 568/335; 562/473

[56] References Cited

U.S. PATENT DOCUMENTS

| | | | |
|---|---|---|---|
| 3,365,448 | 1/1968 | Lesher | 260/240 |
| 3,997,530 | 12/1976 | Fanshawe et al. | 260/240 |
| 5,475,145 | 12/1995 | Chassaing et al. | 568/335 |

FOREIGN PATENT DOCUMENTS

| | | |
|---|---|---|
| 094 239 | 11/1983 | European Pat. Off. . |
| 418 175 | 3/1991 | European Pat. Off. . |
| 2181133 | 4/1987 | United Kingdom . |
| 95/29893 | 11/1995 | WIPO . |
| 95/29898 | 11/1995 | WIPO . |
| 96/02485 | 2/1996 | WIPO . |
| 96/02486 | 2/1996 | WIPO . |

OTHER PUBLICATIONS

Ames, D.E., et al., Synthesis, "Synthesis of 1–Aryl–4–oxo–1H,4H–cinnoline–3–carboxylic Acid Esters", vol. 1, 1983, pp. 52–53.

Grohe, Klaus, et al., Liebigs Ann. Chem., "Cycloaracylation of enamines. I. Synthesis of 4–quinolone–3–carboxylic acids", vol. 1, 1987, pp. 29–37.

Lee–Ruff, E., et al., J. Chem. Soc., Chem. Commun., "Reinvestigation of a Reported Synthesis of a Series of Tetracarbonylmethanes", vol. 3, 1990, pp. 265–266.

*Primary Examiner*—Richard L. Raymond
*Assistant Examiner*—Tamthom N. Truong
*Attorney, Agent, or Firm*—Marian T. Thomson

[57] ABSTRACT

This invention relates to processes for the preparation of aryl-β-diketones and aryl-pyrimidine ketones. In addition, this invention relates to the preparation of aryl-β-triketones and dimethyl aminomethylene β-diketones, which are useful as crop protection intermediates.

3 Claims, No Drawings

PROCESSES FOR THE PREPARATION OF ARYL-β-DIKETONES, ARYLPYRIMIDINE KETONES AND CROP PROTECTION INTERMEDIATES

This invention relates to processes for the preparation of aryl-β-diketones and aryl-pyrimidine ketones. In addition, this invention relates to the preparation of aryl-β-triketones and dimethyl aminomethylene β-diketones, which are useful as crop protection intermediates.

BACKGROUND OF THE INVENTION

Certain substituted-heteroaryl herbicides are described in PCT publication Nos. WO 95/29898 and 95/29893 which are incorporated herein by reference.

One preferred class of these herbicides are substituted-pyrimidines which have the following structure:

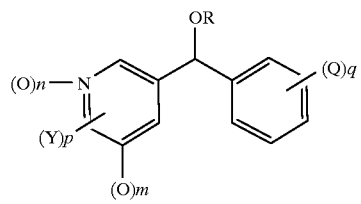

(I)

wherein Q is trifluoromethyl, fluoro, chloro, bromo, iodo, methoxy, methyl, or ethyl; q is 0,1,2,3,4 or 5; and
R is of the formula

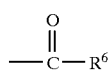

wherein $R^6$ is $C_1$–$C_6$ alkyl or is of the formula $N(R^7)(R^8)$, wherein $R^7$ and $R^8$ are independently hydrogen, $C_1$–$C_6$ haloalkyl, $C_1$–$C_6$ alkyl, $C_2$–$C_6$ alkenyl or together $R^7$ and $R^8$ form a pyrrolidine ring.

Y is halogen, $C_2$–$C_6$ alkenyl, $C_2$–$C_6$ alkynyl, $C_1$–$C_6$ alkyl, $C_1$–$C_6$ haloalkyl, $C_1$–$C_6$ alkoxy, $C_1$–$C_6$ haloalkoxy, nitro, cyano, $C_1$–$C_6$ alkylcarbamylthio, mercapto, hydroxy, thiocyano, $(C_1$–$C_6)$-alkoxy-$(C_1$–$C_6)$alkyl, —$S(O)_k$—$R^{10}$ or —$N(R^{11})(R^{12})$ wherein k is 0, 1 or 2;
$R^{10}$ is $C_1$–$C_6$ alkyl or phenyl;
$R^{11}$ and $R^{12}$ are independently $C_1$–$C_6$ alkyl, $C_1$–$C_6$ alkylthio or $C_1$–$C_6$ alkoxy; n and m are independently 0 or 1 and p is 0, 1, 2, or 3.

As is discussed PCT publication WO 95/29898, compounds of formula I may be made using the following general procedure. First, a benzoyl chloride is reacted with the magnesium enolate of an appropriate β-ketoester to form a triketo intermediate followed by hydrolysis and decarboxylation to a β-diketone intermediate. The diketone is then converted to the alkoxy methylene or dialkylaminomethylene β-diketone by standard methods. Final ring closure to the pyrimidine is accomplished by heating with formamidine acetate in an alcoholic solvent, followed by reduction of the resulting benzoyl pyrimidine, to produce a hydroxybenzyl pyrimidine compound.

Using the above procedure, the decarboxylation reaction to generate the β-diketone intermediate produces an unwanted by-product, namely an aryl methyl ketone. Surprisingly, the inventors have discovered that if the β-keto ester contains an allyl group or a substituted allyl group, the decarboxylation reaction to generate the aryl-β-diketone proceeds without the generation of an aryl methyl ketone. The fact that no aryl methyl ketone is generated greatly reduces the costs of production.

SUMMARY OF THE INVENTION

The present invention provides a process for preparing an aryl-β-diketone of the formula

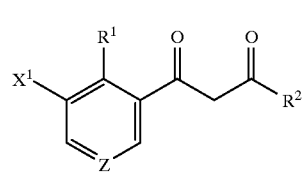

(II)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; and Z is CH or N, comprising:
reacting a compound of the formula

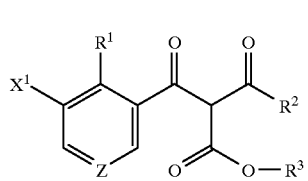

(III)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; and Z is CH or N, with a reducing agent and a metal catalyst.

In another aspect the present invention is directed toward a compound of the formula

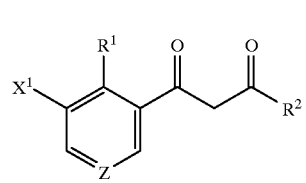

(II)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; and Z is CH or N.

In yet another aspect, the present invention is directed toward the compound of the formula

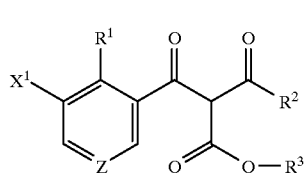

(III)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; and Z is CH or N.

In still yet another aspect, the present invention is directed to a process for preparing an aryl-pyrimidine ketone of the formula

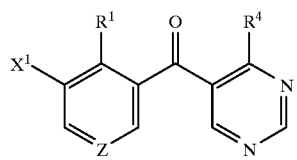

(IV)

wherein $R^1$ is hydrogen, $C_1$–$C_6$ alkyl, $C_1$–$C_6$ haloalkyl, halogen, nitro or $C_2$–$C_4$ alkenyl; $R^4$ is $C_3$–$C_6$ cycloalkyl or hydroxy; $X^1$ is hydrogen, halogen, $C_1$–$C_6$ alkyl or $C_1$–$C_6$ haloalkyl; and Z is CH or N, comprising:

reacting a compound of the formula

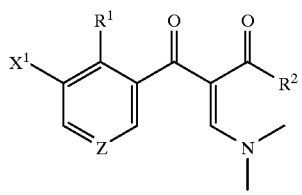

(V)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; and Z is CH or N, with a formamidine salt and a base in an alcoholic solvent.

Finally, this invention is directed to compounds of the formula

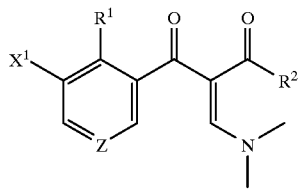

(V)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; and Z is CH or N.

Compounds of Formulae II, III, IV and V have utility as herbicide intermediates. Representative herbicidal compounds generated from said intermediates are shown in Examples 8 and 9.

DETAILED DESCRIPTION OF THE INVENTION

In one aspect, this invention relates to a process for the preparation of aryl-β-diketones as well as the novel aryl-β-diketones themselves. The inventive process can be represented schematically as shown in Scheme I below:

SCHEME I

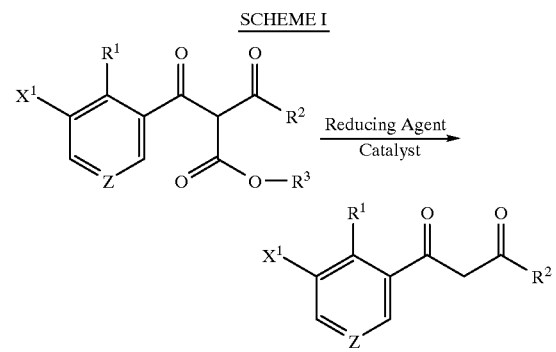

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; and Z is CH or N. Especially preferred products of this process are those in which $R^1$ is trifluoromethyl, $R^2$ is $C_3$ alkyl or cycloalkyl, $R^3$ is allyl or substituted allyl, $X^1$ is hydrogen and Z is CH or N.

In another aspect, this invention relates to the novel aryl-β-triketones of formula III. These compounds may be synthesized using the reaction shown in the following schematic representation:

SCHEME II

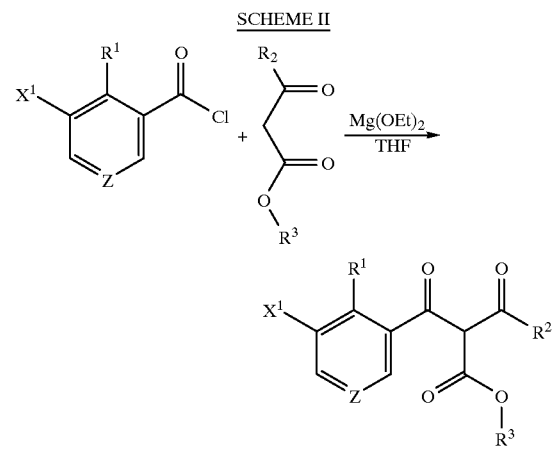

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; and Z is CH or N.

In yet another aspect, this invention relates to the process of preparing an aryl-pyrimidine ketone according to scheme III below:

SCHEME III

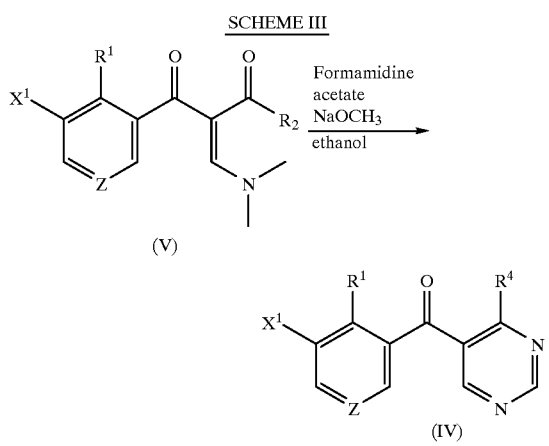

wherein $R^1$ is hydrogen, $C_1$–$C_6$ alkyl, $C_1$–$C_6$ haloalkyl, halogen, nitro or $C_2$–$C_4$ alkenyl; $R^2$ is $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; $R^4$ is $C_3$–$C_6$ cycloalkyl or hydroxy; and Z is CH or N.

A. Formation of aryl-β-triketones:

The aryl-β-triketones of this invention may be generated by reacting an aryl acid chloride with a β-diketone in the presence of magnesium diethoxide to generate an aryl-β-triketone as shown in Scheme II and Example I. In general, the preparation of acyl chlorides and β-diketones are described in J. March, *Advanced Organic Chemistry*, fourth edition, J. Wiley & Sons, New York (1992) pages 437–438 and 490–494 respectively. Typically, a ketoester and $Mg(OEt)_2$ are combined in a suitable solvent, such as tetrahydrofuran, toluene, dioxane or dimethyl formamide or the like, then heated for several hours. The solvent is then evaporated to remove the ethanol. The suitable solvent is replaced, the acid chloride added and the reaction mixture heated to complete the reaction.

As discussed above, $R^3$ is allyl or substituted allyl. The allyl group may be substituted with mono-, di- and poly-halogen, cyano, $C_1$–$C_3$ alkyl, $C_1$–$C_3$ haloalkyl, $C_1$–$C_3$ alkoxy, and phenyl groups.

The term halogen means chlorine, fluorine, bromine and iodine. The term haloalkyl means an alkyl group wherein at least one of the hydrogen atoms is replaced with a halogen atom.

B. Formation of aryl-β-diketones:

The aryl-β-diketones may be generated by the decarboxylation of the aryl-β-triketones prepared in part A. Typically, in a suitable reaction vessel such as a round bottom flask, the aryl-β-triketone is reacted with a reducing agent and a palladium catalyst to generate the aryl-β-diketones. Suitable reducing agents include hydrogen gas, tributyltin hydride and $NaBH_4$. The preferred reducing agents include soluble salts of formic acid such as the combination of formic acid and triethylamine (triethylammonium formate).

If the combination of formic acid and triethylamine are used, preferably a stoichiometric amount of triethylamine and a molar excess of formic acid is used. A three fold molar excess of formic acid is especially preferred.

The preferred palladium catalyst is palladium acetate. A 20 fold molar excess of aryl-β-triketone is used compared to the palladium acetate. Palladium zero catalysts are also quite effective allowing lower amounts of catalyst provided that the reducing agent is readily abundant and available. If the reducing agent is not readily soluble, and therefore not readily available, allyl transfer occurs as in Example 5 part B. This is due in part to the insolubility of ammonium formate in tetrahydrafuran.

A suitable solvent is added, such as tetrahydrofuran, and the reaction mixture, if necessary, is heated to reflux temperature. Although the reflux temperature is dependent upon which solvent is used, when tetrahydrofuran is used, its boiling point is about 66° C. Although tetrahydrofuran is the preferred solvent, other suitable solvents include toluene, dioxane, and dimethylformamide. The temperature is maintained and if necessary the reaction is refluxed for one to three hours. The reaction solvent is then stripped under vacuum. Subsequently, the reaction mixture is extracted with diethyl ether and then washed with water. The organic layer is dried over $MgSO_4$ and evaporated to dryness to generate the aryl-β-diketone in good yield.

C. Formation of aryl-pyrimidine ketone:

The aryl-pyrimidine ketones may be prepared by first reacting the aryl-β-diketones prepared in part B above with dimethylformamide dimethylacetal to generate the dialkylaminomethylene β-diketone compounds of formula V. Analogously, triethyl orthoformate may be used in lieu of dimethylformamide dimethylacetal to generate an ethoxymethylene β-diketone. Subsequent ring closure to the pyrimidine is accomplished by heating the methylene β-diketone intermediate with a formamidine salt and a base in an alcoholic solvent.

In a suitable reaction vessel, an aryl-β-diketone prepared in part B above is reacted with dimethylformamide dimethylacetal in stoichiometric proportions. The solution is stirred and allowed to proceed from about 5 to about 10 hours to generate an dialkylaminomethylene β-diketone intermediate.

The dialkylaminomethylene β-diketone intermediate is added to stoichiometric amounts of a formamidine salt, such as formamidine acetate and a base, such as sodium methoxide, in a $C_1$–$C_6$ alcohol. The mixture is stirred and heated for about 1 hour. Suitable alcoholic solvents include, but are not limited to, methanol and ethanol. Subsequently, the reaction mixture is extracted with methylene chloride and then washed with water. The organic layer is dried over $MgSO_4$ and evaporated to dryness to generate the aryl-pyrimidine ketone.

D. Reduction of the aryl-pyrimidine ketone:

A compound of formula IV prepared in part C may be reduced with a suitable reducing agent such as sodium borohydride, to produce a hydroxybenzyl pyrimidine compound or hydroxynicotinyl pyrimidine compound. If sodium borohydride is used, a 2–4 molar excess of the compound of formula IV is used compared to the sodium borohydride.

Herbicidal derivatives of these hydroxybenzyl pyrimidine or hydroxynicotinyl pyrimidine compounds are produced according to the general procedures which follow. The reduced formula (IV) product, in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as a carbamoyl halide, an alkyl halide, a sulfonyl halide or a phosphoryl halide, or an alkyl or aryl acid halide, or a trialkylsilyl halide) is then added and the mixture agitated until the reaction is complete. The reaction may be quenched by the addition of an aqueous solution, and the products recovered by conventional techniques, such as extraction, filtration and the like. The product so recovered may then be purified by conventional techniques such as flash chromatography or the like.

Alternatively, the reduced product of formula IV in suitable solvent (such as tetrahydrofuran, methylene chloride or the like) may be added to between about 2 and about 3 equivalents of an appropriate isocyanate, such as an alkyl or aryl isocyanate. Between about 1 and about 100 mole percent of one or more appropriate catalysts, e.g., triethyl amine or dibutyl tin dilaurate, may be added and the reaction mixture agitated at between about 0° and 100° C. for an appropriate period (e.g., 2 to 24 hours). The product may be recovered by conventional techniques (such as extraction, filtration or the like) and may be purified by conventional techniques such as flash chromatography or the like.

The following non-limiting examples illustrate the instant invention:

EXAMPLE 1

Preparation of Aryl β-Triketone (A) Preparation of the β-ketoester

To a round bottom flask equipped with an addition funnel and cold water condenser was added, 21.3 grams (0.15 mol.) of diallyl carbonate and 50 mL of tetrahydrofuran and the mixture was stirred. Next, sodium hydride, 8.4 grams (0.21 mol.), was added portion-wise. To the reaction mixture was added, 12.6 grams (0.15 mol.) of cyclopropyl methyl ketone (dissolved in 25 mL of tetrahydrofuran) via the addition funnel. The mixture was heated to relux and heated for an additional 1 hour. Subsequently, the mixture was allowed to cool and the solvent was stripped. Next, cold water (50 mL) and 1 N hydrochloric acid (50 mL) were added. The reaction mixture was transferred to a separatory funnel and diethyl ether was added. The organic layer was dried over $MgSO_4$ and stripped under vacuum to yield the β-ketoester, carboallyloxymethyl cyclopropyl ketone.

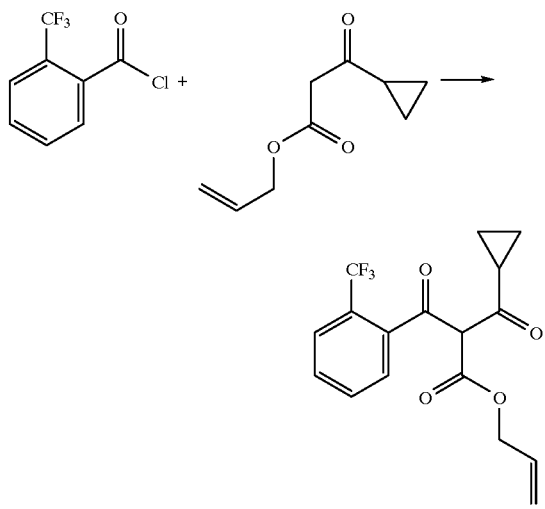

(B) Preparation of aryl β-triketone

To a round bottom flask was added 23.6 grams ( 0.14 mol.) of the β-ketoester, 16 grams ( 0.14 mol.) of magnesium ethoxide and 100 mL of tetrahydrofuran. The reaction mixture was then refluxed for 2 hours and the solvent stripped to insure complete removal of the ethanol by-product. The flask was then recharged with 100 mL of tetrahydrofuran and 29.3 grams (0.14 mol.) of the aryl acid chloride. The solution was refluxed for several hours, after which the mixture was stripped under vacuum, extracted with diethyl ether and washed with water. The 46.4 grams of β-triketone product, trifluoromethylbenzoylcarboallyloxymethyl cyclopropyl ketone were confirmed by infrared (IR) and nuclear magnetic resonance (NMR) spectroscopy and mass spectrometry (MS).

EXAMPLE 2

Preparation of Trifluoromethylbenzoylmethyl Cyclopropyl Ketone

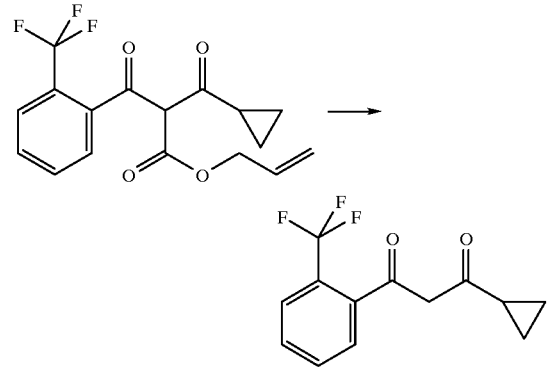

To a round bottom flask was added, 120 grams of β-triketone (0.27 mol.) (generated in Example 1), 450 mL of tetrahydrofuran, 23.3 grams of formic acid (0.62 mol.), 39.2 mL triethylamine (0.28 mol.) and 3 grams of palladium acetate (0.014 mol.). The reaction mixture was stirred and refluxed two hours. Next, an additional 10 mL of formic acid was added and the mixture refluxed for an another hour. Subsequently, 1 gram of palladium acetate and 10 additional mL of formic acid were added.

After an additional hour of reflux, the mixture was stripped under vacuum, extracted with diethyl ether and washed with water. The organic layer was dried over $MgSO_4$ and evaporated to dryness to yield 68.1 grams of the β-diketone, trifluoromethylbenzoylmethyl cyclopropyl ketone. The product was confirmed by infrared (IR) and nuclear magnetic resonance (NMR) spectroscopy and mass spectrometry (MS).

EXAMPLE 3

Preparation of Trifluoromethylnicotinoylmethyl Ethyl Ketone

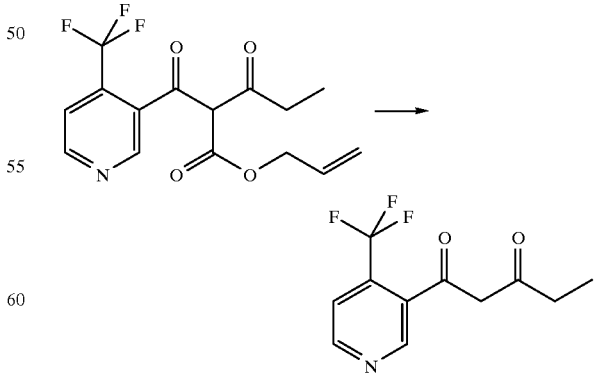

(A) Preparation of aryl β-triketone

To a round bottom flask was added 14.9 grams ( 0.105 mol.) of the β-ketoester (prepared by ester exchange from ethyl propionoyl acetate), 11.3 grams ( 0.1 mol.) of magnesium ethoxide and 150 mL of tetrahydrofuran. The solution was then refluxed for 2 hours and the solvent stripped to ensure complete removal of the ethanol by-product. The flask was then recharged with 100 mL of tetrahydrofuran and 0.095 moles of the acid chloride ( prepared from 20 grams of 4-trifluoromethylnicotinic acid and oxalyl chloride). The solution was returned to reflux for several hours, after which time the reaction was stripped and worked up with dilute acid and ether. The aryl β-triketone product, trifluoromethylnicotinoylcarboallyloxymethyl ethyl ketone (22.7 grams) was confirmed by IR, NMR and MS.

(B) Preparation of trifluoromethyinicotinoylmethyl ethyl ketone

To a round bottom flask was added, 21.1 grams of the β-triketone (0.064 mol.), 110 mL tetrahydrofuran, 10 mL formic acid (0.28 mol.), 9.2 mL triethylamine (0.066 mol.) and 1 gram of palladium acetate (0.0046 mol.). The reaction mixture was stirred and refluxed one hour.

Subsequently, the mixture was stripped under vacuum, extracted with diethyl ether and washed with water. The organic layer was dried over MgSO$_4$ and evaporated to dryness to yield 14.7 grams of the β-diketone, trifluoromethylnicotinoylmethyl ethyl ketone. The product was confirmed by infrared (IR) and nuclear magnetic resonance (NMR) spectroscopy and mass spectrometry (MS).

EXAMPLE 4

Preparation of Trifluoromethyinicotinolymethyl Cyclopropyl Ketone

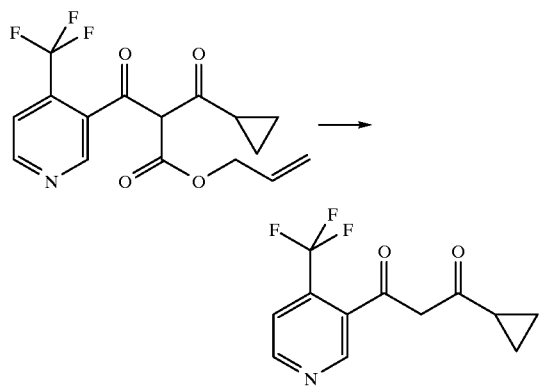

The pyridyl β-triketone in Example 4 was generated using identical reaction conditions as stated in Example 3 starting from trifluoromethylnicotinoyl chloride and the corresponding β-ketoester.

To a round bottom flask was added, 34.8 grams of the β-triketone (0.10 mol.), 175 mL tetrahydrofuran, 8.7 mL of formic acid (0.23 mol.), 14.6 mL triethylamine (0.10 mol.) and 1.1 grams palladium acetate (0.005 mol.). The reaction was stirred and refluxed for 1 hour. One equivalent of formic acid was added and the mixture refluxed an additional hour.

The mixture was stripped under vacuum, extracted with diethyl ether and washed with water. The organic layer was dried over MgSO$_4$ and evaporated to dryness to yield 25 grams of the β-diketone. The product was confirmed by infrared (IR) and nuclear magnetic resonance (NMR) spectroscopy and mass spectrometry (MS).

EXAMPLE 5

Part A. Reducing Agent Soluble in Solvent Used

Preparation of Trifluoromethylbenzoylmethyl Ethyl Ketone Using a Palladium Zero Catalyst

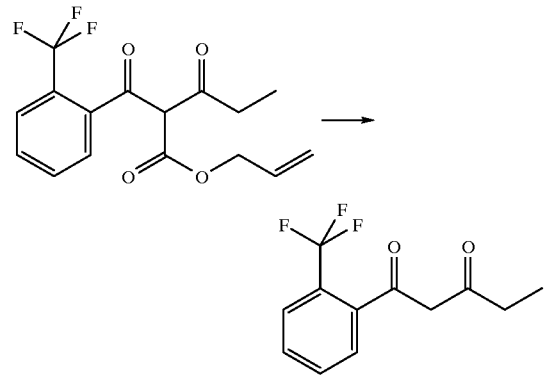

To a round bottom flask was added, 44 grams β-triketone (0.134 mol.), 200 mL tetrahydrofuran, 15.2 mL formic acid (0.402 mol.), 19.1 grams triethylamine (0.137 mol.), and 0.77 grams tetrakis (triphenylphosphine) palladium (0.00067 mol.). The reaction mixture was stirred at ambient temperature for about 72 hours.

The mixture was stripped under vacuum, extracted with diethyl ether and washed with water. The organic layer was dried over MgSO$_4$ and evaporated to dryness to yield 32.2 grams of the β-diketone. The product was confirmed by infrared (IR) and nuclear magnetic resonance (NMR) spectroscopy and mass spectrometry (MS).

Part B. Reducing Agent Insoluble in Solvent Used

Preparation of Trifluoromethylbenzoylbutylene Cyclopropyl Ketone

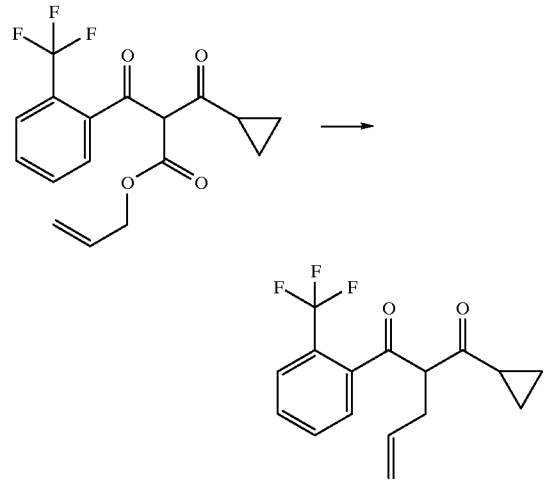

To a round bottom flask was added 5.0 grams (0.0147 mol.) of the aryl β-triketone, combined with 50 mL tetrahydrofuran, 1.85 g (0.029 mol.) of ammonium formate and 0.17 g (0.000147) tetrakis (triphenylphosphine) palladium and the reaction mixture heated to reflux for one half hour. Subsequently, the reaction mixture was cooled to ambient temperature and stirred over night. The mixture was heated to reflux an additional hour the next day and cooled to ambient temperature. The mixture was then stripped under vacuum, extracted with diethyl ether and washed with water. The organic layer was dried over MgSO₄ and evaporated to dryness to yield 3.8 grams of the product. The product was confirmed by infrared (IR) and nuclear magnetic resonance (NMR) spectroscopy and mass spectrometry (MS).

EXAMPLE 6

Preparation of 4-Cyclopropyl-5-[(2-Trifluoromethyl)Benzoyl]-Pyrimidine

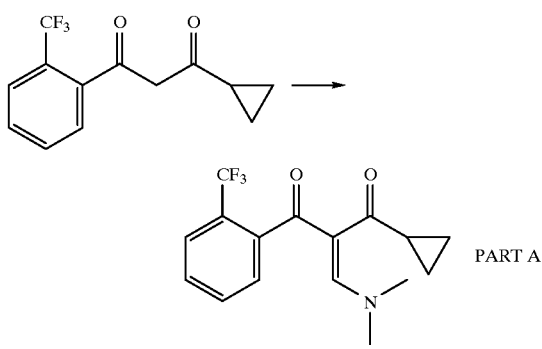

(A) 68.1 grams (0.266 mol.) of trifluoromethylbenzoylmethyl cyclopropyl ketone were combined neat with 39.5 grams (0.297 mole) of N,N-dimethylformamide dimethyl acetal. The solution was stirred for 45 minutes and stripped to yield 82.9 grams of trifluoromethylbenzoyl-methyl [(dimethylamino)methylene] cyclopropyl ketone. The product was confirmed by infrared (IR) and nuclear magnetic resonance (NMR) spectroscopy and mass spectrometry (MS).

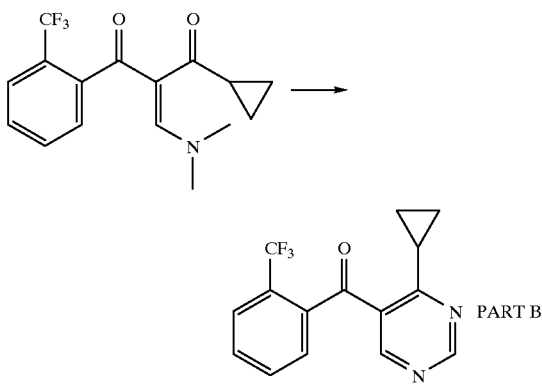

(B) To a refluxing solution of 56.9 grams (0.547 mol.) formamidine acetate, 700 mL of ethanol and 125 mL (0.547 mol.) of a 25% sodium methoxide in methanol solution was added dropwise, 82.9 grams (0.267 mol.) of the product in step A. Next, the reaction mixture was refluxed 4 hours and allowed to stir over the weekend. The reaction mixture was subsequently evaporated under reduced pressure and extracted with 20 mL of dichloromethane. The evaporated product was chromatographed on a column 4 inches high and 3 inches in diameter of silica gel, with 75 mL fractions of ethyl acetate mixed with hexanes. Twenty-two fractions of 20% ethyl acetate were collected, then sixteen fractions of 50% ethyl acetate were collected. Fractions 8 through 13 were collected to yield 40.5 grams of the product, 4-cyclopropyl-5-[(2-trifluoromethyl)benzoyl]-pyrimidine.

EXAMPLE 7

Preparation of 4-Cyclopropyl-5-[2,3 Dichlorobenzoyl]-Pyrimidine

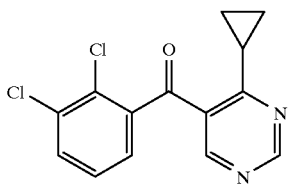

(A) Preparation of the β-ketoester

To a round bottom flask equipped with an addition funnel and cold water condenser was added, 21.3 grams (0.15 mol.) of diallyl carbonate and 50 mL of tetrahydrofuran and the mixture was stirred. Next, sodium hydride, 8.4 grams (0.21 mol.), was added portion-wise. To the reaction mixture was added, 12.6 grams (0.15 mol.) of cyclopropyl methyl ketone (dissolved in 25 mL of tetrahydrofuran) via the addition funnel. The mixture was heated to relux and heated for an additional 1 hour. Subsequently, the mixture was allowed to cool and the solvent was stripped. Next, cold water (50 mL) and 1 N hydrochloric acid (50 mL) were added. The reaction mixture was transferred to a separatory funnel and diethyl ether was added. The organic layer was dried over MgSO₄ and stripped under vacuum to yield the β-ketoester, carboallyloxymethyl cyclopropyl ketone.

(B) Preparation of aryl β-triketone

To a round bottom flask was added 16.8 grams (0.1 mol.) of the β-ketoester, 11.4 grams of magnesium ethoxide and 100 mL of tetrahydrofuran. The reaction mixture was then refluxed for 2 hours and the solvent stripped to insure complete removal of the ethanol by-product. The flask was then recharged with 100 mL of tetrahydrofuran and 20.85 grams (0.1 mol.) of the 2,3 dichlorobenzoyl chloride. The solution was refluxed for two hours, after which the mixture was stripped under vacuum, extracted with diethyl ether and dried with magnesium sulfate. The 30 grams of product, 2,3 dichlorobenzoylcarboallyloxymethyl cyclopropyl ketone were confirmed by infrared (IR) and nuclear magnetic resonance (NMR) spectroscopy and mass spectrometry (MS).

(C) Preparation of 2,3 dichlorolbenzoylmethyl cyclopropyl ketone

To a round bottom flask was added, 34.1 grams of the β-triketone (part B) (0.1 mol.), 450 mL of tetrahydrofuran, 14.55 grams of formic acid (0.39 mol.), 21 mL triethylamine (0.15 mol.) and 0.5 grams of palladium acetate (0.002 mol.). The reaction mixture was stirred and refluxed six hours. Next, an additional 50% more of formic acid and palladium acetate was added and the mixture refluxed for four (4) more hours. The mixture was stripped under vacuum, extracted with diethyl ether and 1 N hydrochloric acid. The mixture was then washed with water. The organic layer was dried over MgSO₄ and evaporated to dryness to yield the β-diketone. The product was confirmed by infrared (IR) and nuclear magnetic resonance (NMR) spectroscopy and mass spectrometry (MS).

(D) Preparation of 2,3 dichlorobenzoyl-methyl [(dimethylamino)methylene] cyclopropyl ketone 29 grams (0.113 mol.) of 2,3-dichlorobenzoylmethyl cyclopropyl ketone were combined neat with 20.2 grams (0.169 mole) of N,N-dimethylformamide dimethyl acetal. The solution was stirred for 48 hours and stripped to yield 42 grams of 2,3-dichlorobenzoylmethyl[(dimethylamino) methylene] cyclopropyl ketone.

(E) Preparation of 4-cyclopropyl-5-[2,3 dichlorobenzoyl]-pyrimidine

To a refluxing solution of 20.2 grams (0.169 mol.) formamidine acetate, 200 mL of ethanol and 55.2 grams (0.207 mol.) of a 25% sodium methoxide in methanol solution was added dropwise, 42.3 grams (0.137 mol.) of the dimethylamino-methylene β-diketone. Next, the reaction mixture was refluxed 1.5 hours and allowed to stir over night. The reaction mixture was subsequently evaporated under reduced pressure and extracted with 20 mL of dichloromethane. The evaporated product was chromatographed using ethyl acetate mixed with hexanes. Fractions were collected to yield 39.7 grams of the product, 4-cyclopropyl-5-[2,3 dichlorobenzoyl]-pyrimidine.

EXAMPLE 8

Preparation of 4-Cyclopropyl-5-(1-Benzyloxy-2'-Trifluoromethylbenzyl)-Pyrimidine

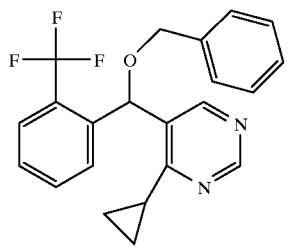

(A) To a solution of 4-cyclopropyl-5-[(2-trifluoromethyl)-benzoyl]-pyrimidine (44.6 grams, 0.153 mol.) (Example 6, Part B) dissolved in 250 mL of ethanol at ambient temperature was added 2.37 grams (0.0622 mol.) of sodium borohydride. Chromatography showed the reaction to be complete 15 minutes after the addition. The mixture was evaporated under reduced pressure, extracted with dichloromethane, washed with water, dried over magnesium sulfate and evaporated under reduced pressure to yield 42.2 grams of the product, 4-cyclopropyl-5-(1-hydroxy-2'-trifluoromethylbenzyl)-pyrimidine.

(B) 1.2 grams (0.00408 mol.) of 4-cyclopropyl-5-(1-hydroxy-2'-trifluoromethylbenzyl)-pyrimidine were combined with 0.59 mL (0.0051 mol.) of benzyl chloride in 12 mL DMF. Sodium hydride 0.11 grams (0.0047 mol.) was added portionwise. The reaction, which was complete in 1 hour, was poured over ice, extracted with dichloromethane, dried over MgSO$_4$, filtered and evaporated to dryness under reduced pressure to yield, 4-cyclopropyl-5-(1-benzyloxy-2'-trifluoromethylbenzyl)-pyrimidine. The product was chromatographed on a 1 inch diameter by 4 inch silica gel column with 50% ethyl acetate/hexanes of which 20 mL fractions were collected. Fractions 4 and 8 were combined and evaporated to yield 0.75 g of the product.

EXAMPLE 9

Preparation of 4-Cyclopropyl-5-(1-Benzyloxy-2'-Trifluoromethylnicotinyl)-Pyrimidine

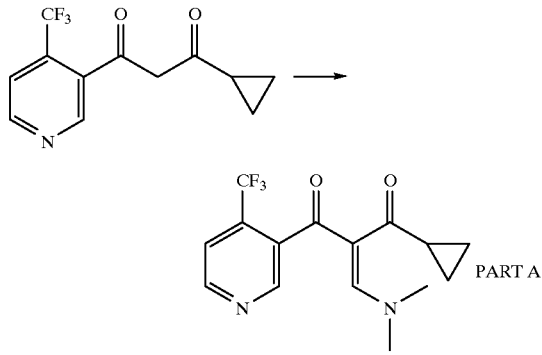

(A) 25grams (0.097mol.) of trifluoromethyinicotinoylmethyl cyclopropyl ketone (Example 4) were combined neat with 14.5 mL (0.109 mole) of N,N-dimethylformamide dimethyl acetal. The solution was stirred for 45 minutes and stripped to yield 27.9 grams of trifluoromethyinicotinoylmethyl[(dimethylamino)-methylene]cyclopropyl ketone. The product was confirmed by infrared (IR) and nuclear magnetic resonance (NMR) and mass spectrometry (MS).

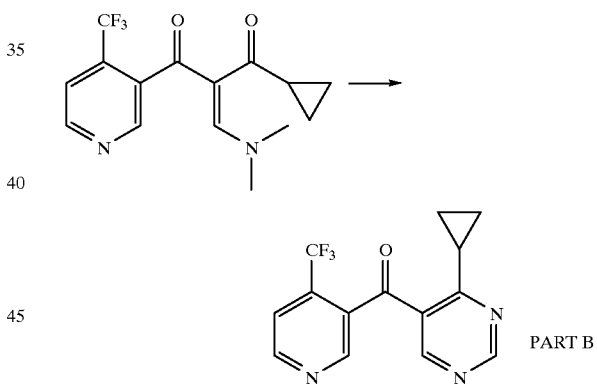

(B) To a refluxing solution of 19.1 grams (0.184 mol.) formamidine acetate, 230 mL of ethanol and 42 mL (0.184 mol.) of a 25% sodium methoxide in methanol solution was added dropwise, 27.9 grams (0.089 mol.) of the product in step A. Next, the reaction mixture was refluxed 4 hours and allowed to stir over the weekend. The reaction mixture was subsequently evaporated under reduced pressure and extracted with 20 mL of dichloromethane. The evaporated product was chromatographed on a column 2 inches high and 4 inches in diameter of silica gel, with 50 mL fractions of ethyl acetate mixed with hexanes. The fractions containing product were collected, to yield 8.4 grams of the product, 4-cyclopropyl-5-[(2-trifluoromethyl)nicotinoyl]-pyrimidine. The product was confirmed by infrared (IR) and nuclear magnetic resonance (NMR) and mass spectrometry (MS).

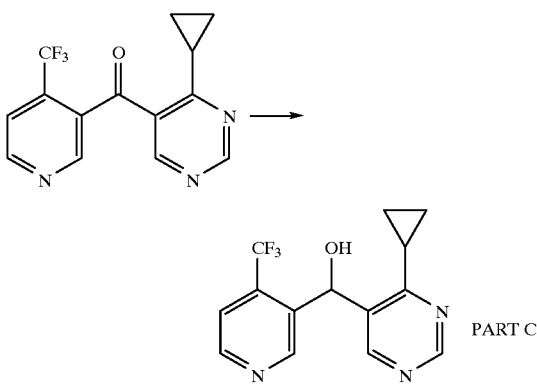

PART C (C) To a solution of 4-cyclopropyl-5-[(2-trifluoromethyl) nicotinoyl]-pyrimidine (8.4grams, 0.0285 mol.) dissolved in 85 mL of ethanol at ambient temperature was added 0.44 grams (0.0119 mol.) of sodium borohydride. Chromatography showed the reaction to be complete 15 minutes after the addition. The mixture was evaporated under reduced pressure, extracted with dichloromethane, washed with water, dried over magnesium sulfate and evaporated under reduced pressure to yield 7.3 grams of the product, 4-cyclopropyl-5-[1-hydroxy-1-(4'-trifluoromethylpyridin-3-yl)]methylpyrimidine. The product was confirmed by infrared (IR) and nuclear magnetic resonance (NMR) and mass spectrometry (MS).

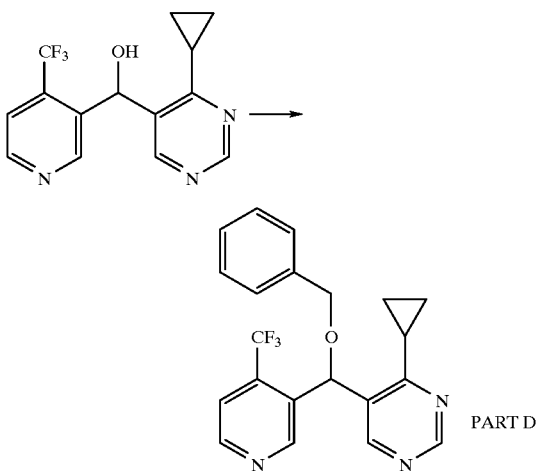

PART D (D)1.5 grams (0.0051 mol.) of 4-cyclopropyl-5-[1-hydroxy-1-(4'-trifluoromethylpyridin-3-yl)]methyl pyrimidine were combined with 0.73 mL (0.00635 mol.) of benzyl chloride in 15 mL DMF. Sodium hydride 0.14 grams (0.00577 mol.) was added portionwise. The reaction, which was complete in 1 hour, was poured over ice, extracted with dichloromethane, dried over MgSO4, filtered and evaporated to dryness under reduced pressure to yield, 4-cyclopropyl-5-(1-benzyloxy-1-(4'-trifluoromethylpyridin-3-yl)methyl pyrimidine. The product was chromatographed on a 2 inch diameter by 4 inch silica gel column with 50% ethyl acetate/hexanes of which 50 mL fractions were collected. The fractions containing product were combined and evaporated to yield 0.3 grams of the product. The product was confirmed by infrared (IR) and nuclear magnetic resonance (NMR) and mass spectrometry (MS).

Although the instant invention has been described with reference to the preferred embodiments and examples thereof, the scope of the present invention is not limited only to the described embodiments. As will be apparent to persons skilled in the art, modifications and adaptations to the above described invention can be made without departing from the spirit and scope of the invention, which is defined and circumscribed by the appended claims.

What is claimed is:

1. A compound of the formula

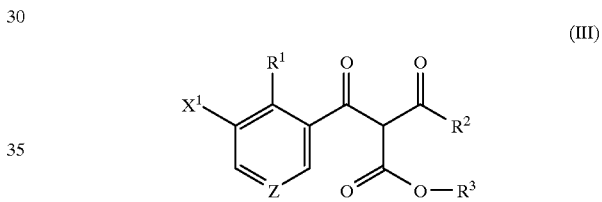

(III)

wherein $R^1$ is hydrogen, $C_1$–$C_6$ alkyl, $C_1$–$C_6$ haloalkyl, halogen, nitro or $C_2$–$C_4$ alkenyl; $R^2$ is $C_1$–$C_6$ alkyl, $C_3$–$C_6$ cycloalkyl or $C_1$–$C_6$ alkoxy; $X^1$ is hydrogen, halogen, $C_1$–$C_6$ alkyl or $C_1$–$C_6$ haloalkyl; $R^3$ is allyl or substituted allyl; and Z is CH.

2. A compound according to claim 1, wherein $R^1$ is $C_1$–$C_6$ haloalkyl; $R^2$ is methyl, isopropyl or cyclopropyl; $R^3$ is allyl or substituted allyl; and Z is CH.

3. A compound according to claim 2, wherein $R^1$ is trifluoromethyl.

* * * * *